(12) United States Patent
Lomeli et al.

(10) Patent No.: US 10,758,288 B2
(45) Date of Patent: Sep. 1, 2020

(54) CORTICAL RIM-SUPPORTING INTERBODY DEVICE

(71) Applicant: DePuy Synthes Products, Inc., Raynham, MA (US)

(72) Inventors: Roman Lomeli, Plymouth, MA (US); Kevin Lee, Canton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 162 days.

(21) Appl. No.: 15/990,513

(22) Filed: May 25, 2018

(65) Prior Publication Data

US 2018/0271576 A1   Sep. 27, 2018

Related U.S. Application Data

(63) Continuation of application No. 14/039,628, filed on Sep. 27, 2013, now abandoned.

(Continued)

(51) Int. Cl.
*A61F 2/44* (2006.01)
*A61B 17/88* (2006.01)
(Continued)

(52) U.S. Cl.
CPC ...... *A61B 17/8855* (2013.01); *A61B 17/7097* (2013.01); *A61B 17/8811* (2013.01); *A61F 2/441* (2013.01); *A61F 2/442* (2013.01); *A61F 2/4455* (2013.01); *A61F 2/4611* (2013.01); *A61F 2002/2817* (2013.01);
(Continued)

(58) Field of Classification Search
CPC .. A61B 17/8852; A61B 17/8855; A61F 2/441
See application file for complete search history.

(56) References Cited

U.S. PATENT DOCUMENTS 6,049,026 A   4/2000   Muschler
6,332,894 B1 *  12/2001   Stalcup .............. A61B 17/7097
                                                    623/17.11
(Continued)

FOREIGN PATENT DOCUMENTS

ES          2094077 A1 *  1/1997   ............. A61F 2/441

OTHER PUBLICATIONS

Hou and Yuan, Influences of disc degeneration and bone mineral density on the structural properties of lumbar end plates, *Spine Journal*, 12, 3, pp. 249-256, 2012.

(Continued)

*Primary Examiner* — Zade Coley

(57) ABSTRACT

A central inflatable distractor and a perimeter balloon are inserted into the disc space in uninflated configurations. The central inflatable distractor is then expanded, thereby distracting the vertebral endplates to the controlled height of the central inflatable distractor. The perimeter balloon is then inflated with a curable substance. The perimeter balloon expands as it is filled with the curable substance and conforms to the void remaining in the disc space around the central inflatable distractor, thereby creating a horseshoe shape. Once the flowable material in the perimeter balloon has cured, the central inflated distractor can be deflated and removed. The remaining void (or inner space) is then packed with graft for fusion.

7 Claims, 17 Drawing Sheets

Related U.S. Application Data

(60) Provisional application No. 61/838,604, filed on Jun. 24, 2013.

(51) Int. Cl.
*A61F 2/46* (2006.01)
*A61B 17/70* (2006.01)
*A61F 2/28* (2006.01)
*A61F 2/30* (2006.01)

(52) U.S. Cl.
CPC . *A61F 2002/2835* (2013.01); *A61F 2002/302* (2013.01); *A61F 2002/30006* (2013.01); *A61F 2002/30011* (2013.01); *A61F 2002/30016* (2013.01); *A61F 2002/30062* (2013.01); *A61F 2002/30069* (2013.01); *A61F 2002/30131* (2013.01); *A61F 2002/30235* (2013.01); *A61F 2002/30331* (2013.01); *A61F 2002/30556* (2013.01); *A61F 2002/30563* (2013.01); *A61F 2002/30579* (2013.01); *A61F 2002/30581* (2013.01); *A61F 2002/30583* (2013.01); *A61F 2002/30586* (2013.01); *A61F 2002/30588* (2013.01); *A61F 2002/444* (2013.01); *A61F 2002/4435* (2013.01); *A61F 2002/4445* (2013.01); *A61F 2310/00023* (2013.01); *A61F 2310/00029* (2013.01); *A61F 2310/00293* (2013.01); *A61F 2310/00353* (2013.01); *A61F 2310/00359* (2013.01); *A61F 2310/00365* (2013.01); *A61F 2310/00371* (2013.01)

(56) References Cited

U.S. PATENT DOCUMENTS

| | | | | |
|---|---|---|---|---|
| 6,805,715 B2* | 10/2004 | Reuter | ............... | A61F 2/441 623/17.12 |
| 6,932,843 B2* | 8/2005 | Smith | ............... | A61B 17/8811 623/17.11 |
| 7,201,774 B2* | 4/2007 | Ferree | ............... | A61F 2/441 623/17.11 |
| 7,699,894 B2* | 4/2010 | O'Neil | ............... | A61F 2/4657 623/17.12 |
| 8,007,535 B2* | 8/2011 | Hudgins | ............... | A61F 2/441 623/17.12 |
| 9,216,098 B2* | 12/2015 | Trudeau | ............... | A61F 2/4657 |
| 2002/0165542 A1* | 11/2002 | Ferree | ............... | A61B 17/1671 606/53 |
| 2003/0028251 A1* | 2/2003 | Mathews | ............... | A61B 17/025 623/17.16 |
| 2003/0220695 A1* | 11/2003 | Sevrain | ............... | A61F 2/442 623/17.16 |
| 2004/0059417 A1* | 3/2004 | Smith | ............... | A61B 17/8811 623/17.11 |
| 2004/0230309 A1* | 11/2004 | DiMauro | ............... | A61L 27/3847 623/17.12 |
| 2005/0027358 A1* | 2/2005 | Suddaby | ............... | A61F 2/441 623/17.11 |
| 2005/0090901 A1* | 4/2005 | Studer | ............... | A61F 2/441 623/17.12 |
| 2005/0119752 A1* | 6/2005 | Williams | ............... | A61F 2/441 623/17.16 |
| 2005/0251259 A1 | 11/2005 | Suddaby | | |
| 2007/0255406 A1 | 11/2007 | Trieu | | |
| 2009/0182343 A1* | 7/2009 | Trudeau | ............... | A61F 2/4657 606/102 |
| 2009/0222093 A1* | 9/2009 | Liu | ............... | A61F 2/442 623/17.12 |
| 2009/0222097 A1* | 9/2009 | Liu | ............... | A61F 2/441 623/17.16 |
| 2010/0256766 A1* | 10/2010 | Hibri | ............... | A61F 2/441 623/17.16 |
| 2011/0004307 A1 | 1/2011 | Ahn | | |
| 2011/0137317 A1 | 6/2011 | O'Halloran | | |
| 2011/0202062 A1 | 8/2011 | O'Halloran | | |
| 2011/0270399 A1* | 11/2011 | Yurek | ............... | A61F 2/441 623/17.16 |
| 2012/0310352 A1* | 12/2012 | DiMauro | ............... | A61L 27/52 623/17.16 |
| 2014/0172105 A1 | 6/2014 | Frasier | | |

OTHER PUBLICATIONS

Pederson, "Thermal assembly of a biometric mineral/collagen composite", *Biomaterials* 24: pp. 4881-4890 (2003).

* cited by examiner

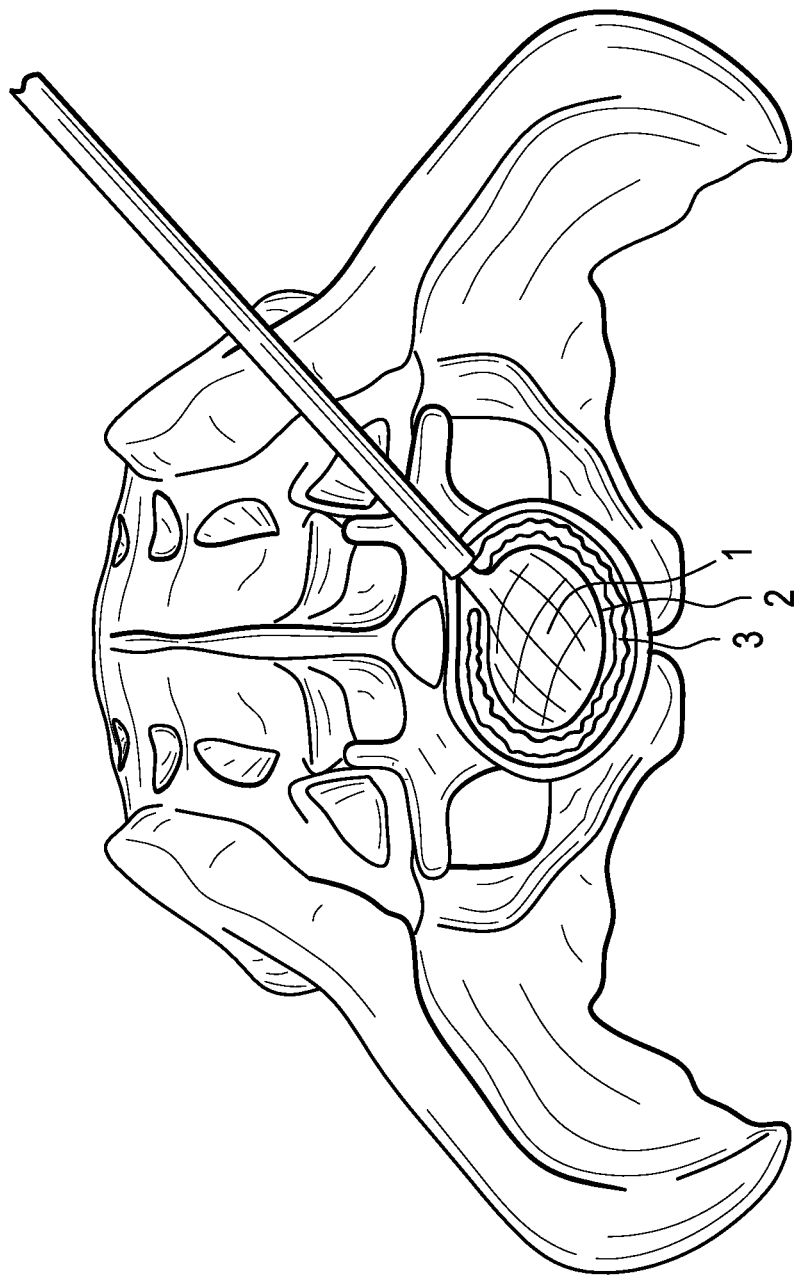

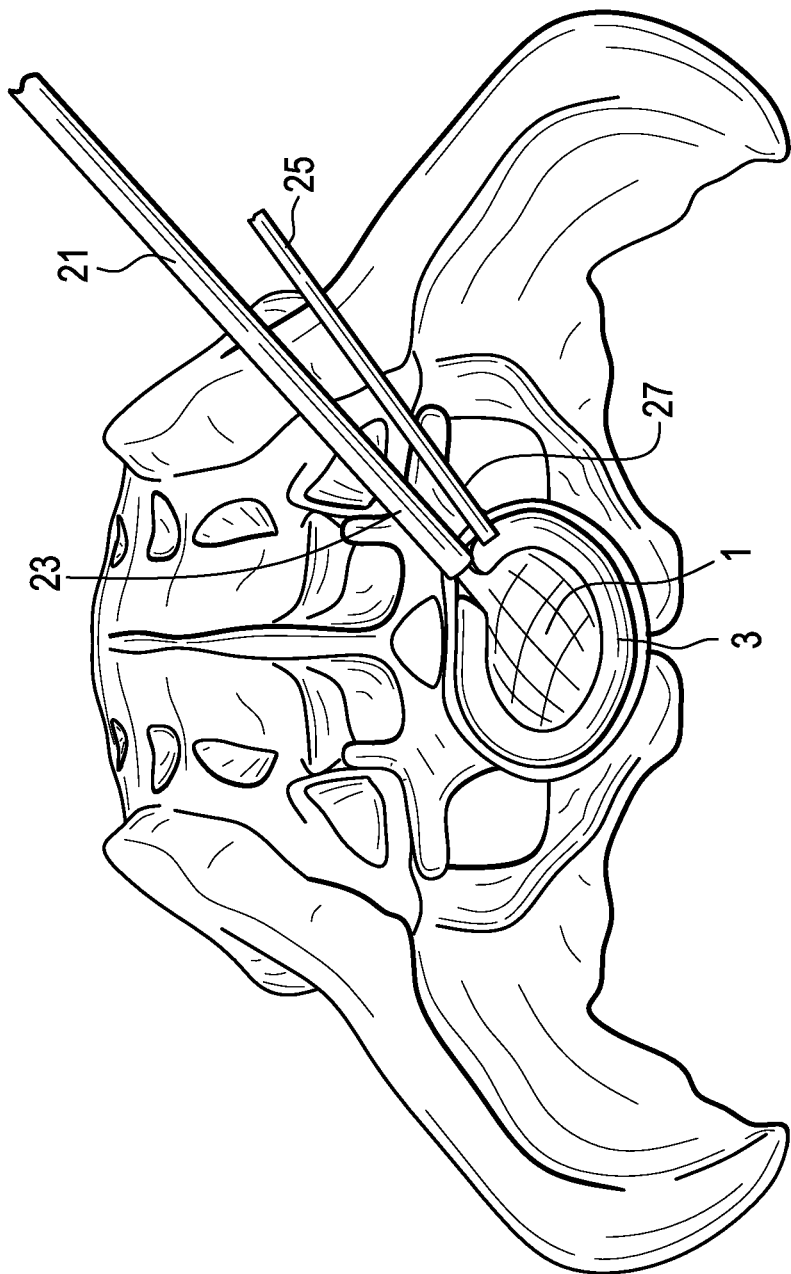

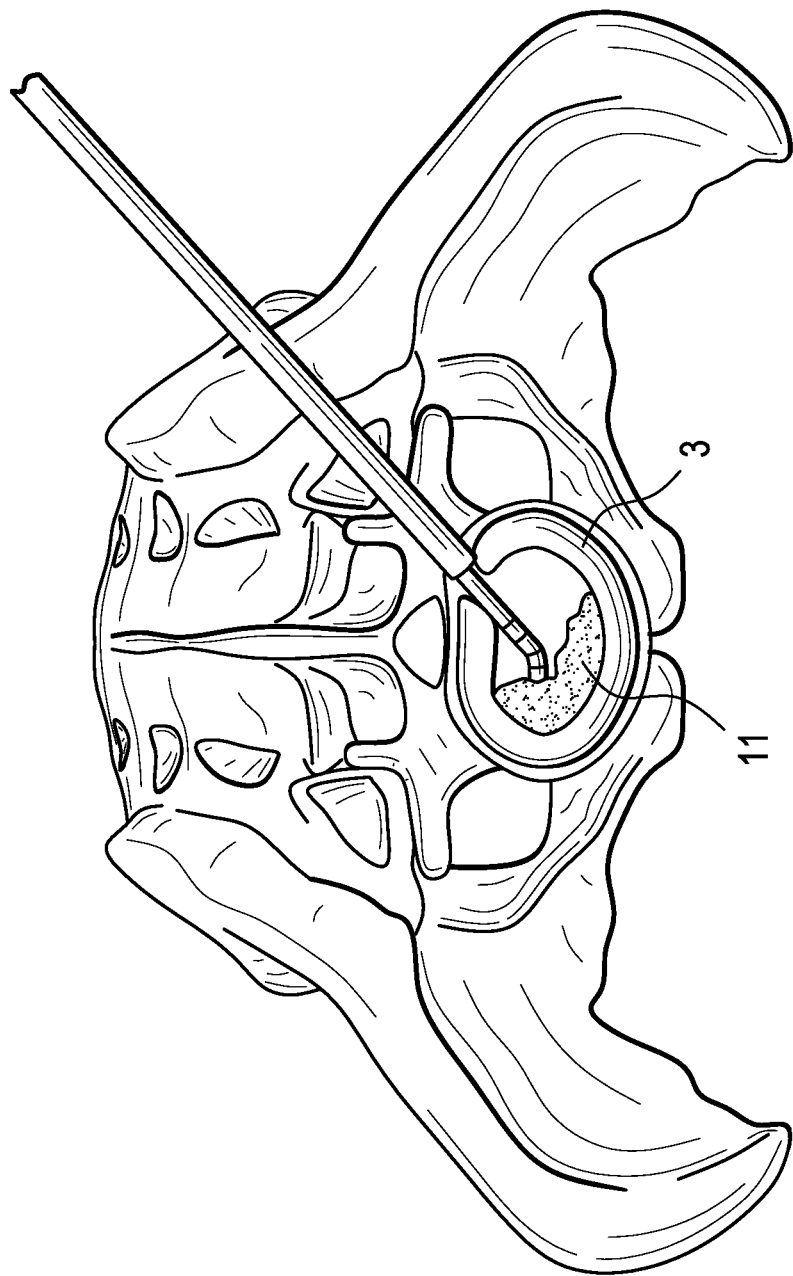

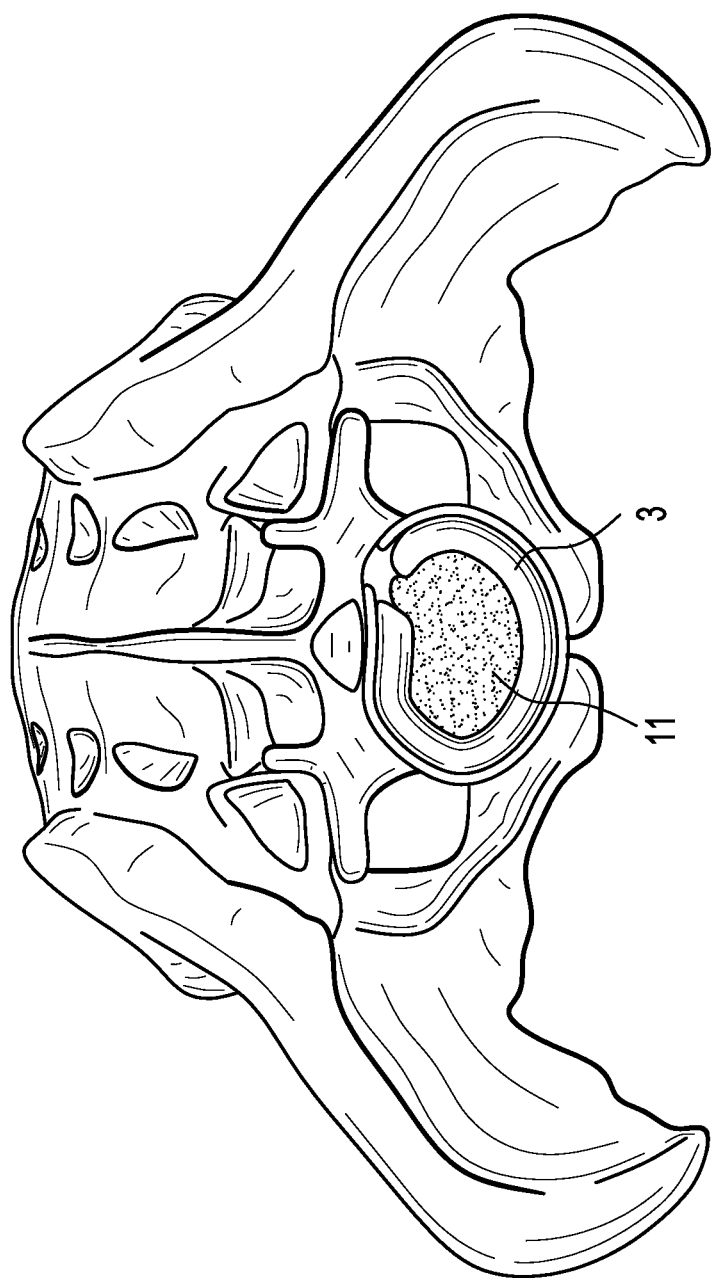

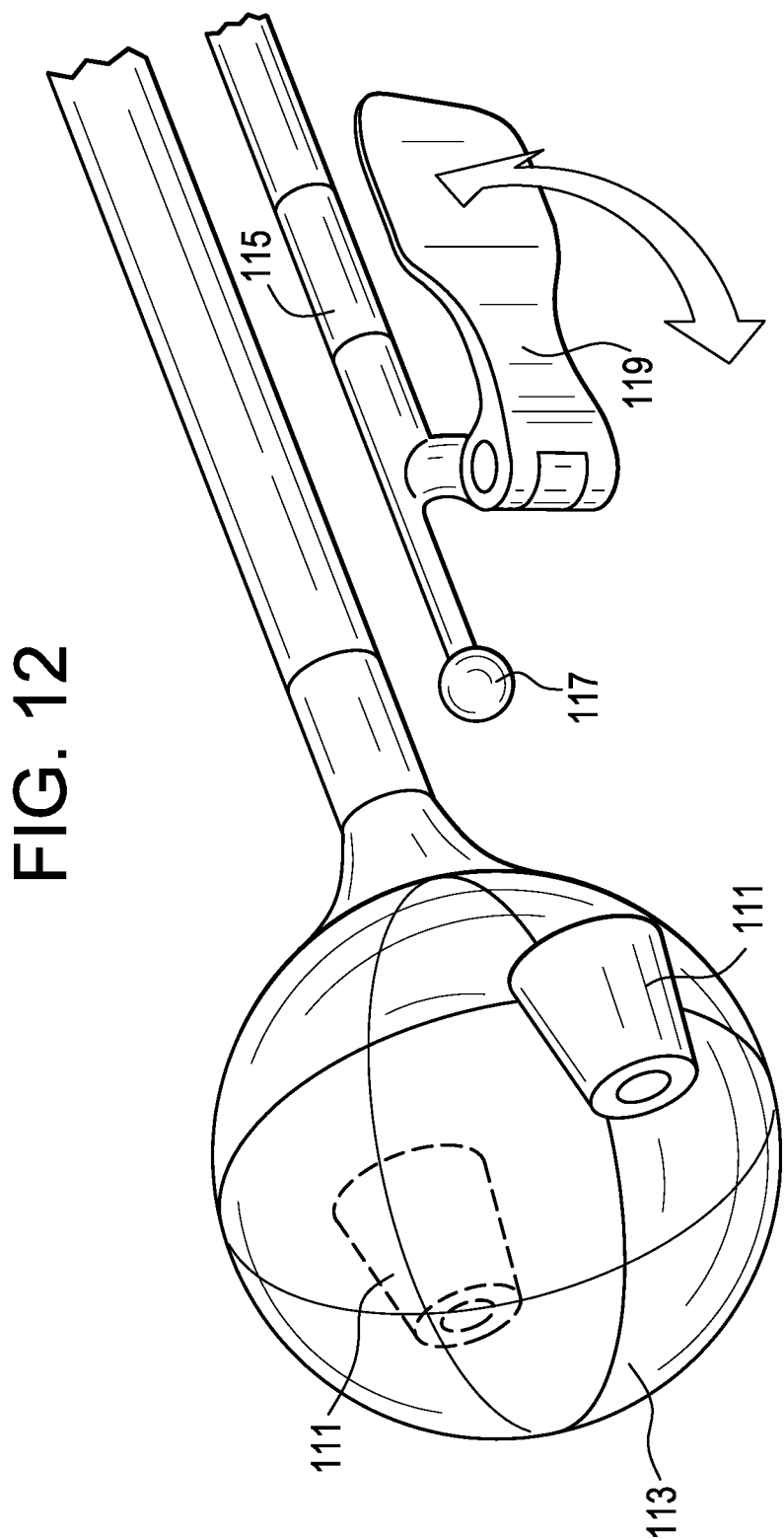

CORTICAL RIM-SUPPORTING INTERBODY DEVICE

CONTINUING DATA

This application claims priority from co-pending U.S. Ser. No. 14/039,628, filed Sep. 27, 2013, entitled "Cortical Rim-Supporting Interbody Device", Lomeli et al, which claims priority from provisional application No. 61/838,604, filed Jun. 24, 2013, Lomeli et al the specifications of which are incorporated by reference in their entirety.

BACKGROUND OF THE INVENTION

In an effort to treat low back pain, surgeon have removed the degenerative disc and inserted a fusion cage into the disc space. In an effort to minimize the invasiveness of the fusion procedure, more recent efforts have focused upon forming the fusion cage in-situ by flowing a curable material into a balloon that has been placed into the disc space.

US Patent Publication 2004-0230309 (DePuy Spine) discloses an orthopedic device for implanting between adjacent vertebrae comprising: an arcuate balloon and a hardenable material within said balloon. In some embodiments, the balloon has a footprint that substantially corresponds to a perimeter of a vertebral endplate. An inflatable device is inserted through a cannula into an intervertebral space and oriented so that, upon expansion, a natural angle between vertebrae will be at least partially restored. At least one component selected from the group consisting of a load-bearing component and an osteobiologic component is directed into the inflatable device through a fluid communication means. The FIG. 6B thereof discloses adjacent balloons in a disc space.

U.S. Pat. No. 8,007,535 (Hudgins) discloses an injectable annular ring useful in treating a deteriorating spinal disc. When used, the annular ring may be collapsed or folded in order for it to be placed through a small opening in a prepared intervertebral space within the annulus using minimally invasive techniques. Deployment or unfolding the ring in the intervertebral space provides an interior cavity bordered by the ring that is in direct contact with the vertebral endplates. When an internal volume of the ring is injected or filled with a load-bearing, hardenable material, the filled ring maintains the intervertebral spacing and prevents the ring from being expelled from the interior cavity through the small annular opening.

U.S. Pat. No. 6,332,894 (Stalcup) discloses an orthopaedic implant for implanting between adjacent vertebrae and a spine, includes a generally annular bag; and a hardened polymer within the bag. The method of fusing adjacent vertebrae in a spine includes the steps of forming an access hole in an annulus of a disc between the adjacent vertebrae; removing the nucleus within the disc to form a cavity surrounded by the annulus; placing a generally annular bag within the cavity; filling the bag with a polymer; injecting bone particles into the cavity surrounded by the annular bag; and hardening the polymer.

US Published Patent Application 2003-0028251 (Mathews) discloses methods and instruments for preparing a disc space and for forming interbody devices therein. The instruments include distractors having enlargeable portions positionable in the disc space for distracting the disc space. The enlargeable portions can also provide form about or against which an interbody device of a first material is placed. A second material may be placed in the disc space previously occupied by the distractors.

US Published Patent Application 2005-0119752 (Williams) discloses devices and methods for manufacturing devices for treating degenerated and/or traumatized intervertebral discs. Artificial discs and components of discs may include an artificial nucleus and/or an artificial annulus and may be comprised of shape memory materials synthesized to achieve desired mechanical and physical properties. An artificial nucleus and/or annulus according to the invention may comprise one or more hollow bodies that may be filled with a curable material for deployment. A hollow body according to the invention may comprise one or more partitions to define one or more chambers and may comprise means for directing the flow of material within said hollow body. FIG. 19a of Williams discloses a two-balloon design comprising a central balloon and a perimeter balloon.

Subsidence of an implanted interbody cage is a known risk in fusion and there is a higher occurrence for patients with lower bone density. Hou and Yuan, *Spine Journal*, 12, 3, 249-256 (2012) investigated the structural properties of lumbar endplates and reported that the periphery of the endplates particularly in the posterolateral region near the pedicles were significantly stronger than the central region. They also concluded that with increasing disc degeneration, the central region became weaker while minimal strength changes were observed in the peripheral region.

SUMMARY OF THE INVENTION

It is an object of the present invention to percutaneously deliver a peripheral structural support element that can sustain loads immediately after surgery while allowing a central graft column to form a complete fusion. The present invention relates to a percutaneous delivery of a large footprint structural support that contacts substantially only the apophyseal ring of the endplates.

In accordance with the present invention, a central inflatable distractor and a perimeter balloon are inserted into the disc space in uninflated configurations. The central inflatable distractor is then expanded, thereby distracting the vertebral endplates to the controlled height of the central inflatable distractor.

The perimeter balloon is then inflated with a curable substance. The perimeter balloon expands as it is filled with the curable substance and conforms to the void remaining in the disc space around the central inflatable distractor, thereby creating a horseshoe shape.

Once the flowable material in the perimeter balloon has cured, the central inflated distractor can be deflated and removed. The remaining void (or inner space) is then packed with graft for fusion.

Therefore in accordance with the present invention, there is provided an instrument for forming an intervertebral fusion device comprising:
a) a distraction device comprising i) a first tube having a distal end portion and ii) an inflatable distractor attached to the distal end portion of the first tube, wherein the inflatable distractor is filled with a biological inert fluid,
b) a fusion assembly comprising i) a second tube having a distal end portion and ii) an inflatable balloon attached to the distal end portion of the second tube, wherein the inflatable balloon is filled with a curable material and has a height sized to span a disc space,
wherein the distal end portion of the first tube is substantially adjacent the distal end portion of the second tube.

Therefore in accordance with the present invention, there is provided a balloon assembly for treating an intervertebral disc space, comprising:
a) an inflated distractor having an outer perimeter and being sized to distract the intervertebral disc space, the inflated distractor filled with a biologically inert fluid,
b) an inflated fusion balloon forming a shape having an outer perimeter and an inner surface, the fusion balloon filled with a curable material,
wherein the balloon wraps around the distractor so that the inner surface of the fusion balloon contacts the outer perimeter of the inflated distractor.

Therefore in accordance with the present invention, there is provided a balloon assembly for treating an intervertebral disc space, comprising:
a) a deflated distractor having an outer perimeter,
b) an inflated fusion balloon forming a shape having an outer perimeter and an inner surface defining an inner space, the fusion balloon filled with a cured material, the balloon being sized to distract the intervertebral disc space,
wherein the deflated distractor is disposed within the inner space of the balloon.

DESCRIPTION OF THE FIGURES

FIGS. 1A-I disclose the step-wise process for making an in-situ formed device in accordance with the present invention.

FIG. 12 discloses an inflated balloon having a docking port for docking an instrument.

DETAILED DESCRIPTION OF THE INVENTION

Figure 1A:
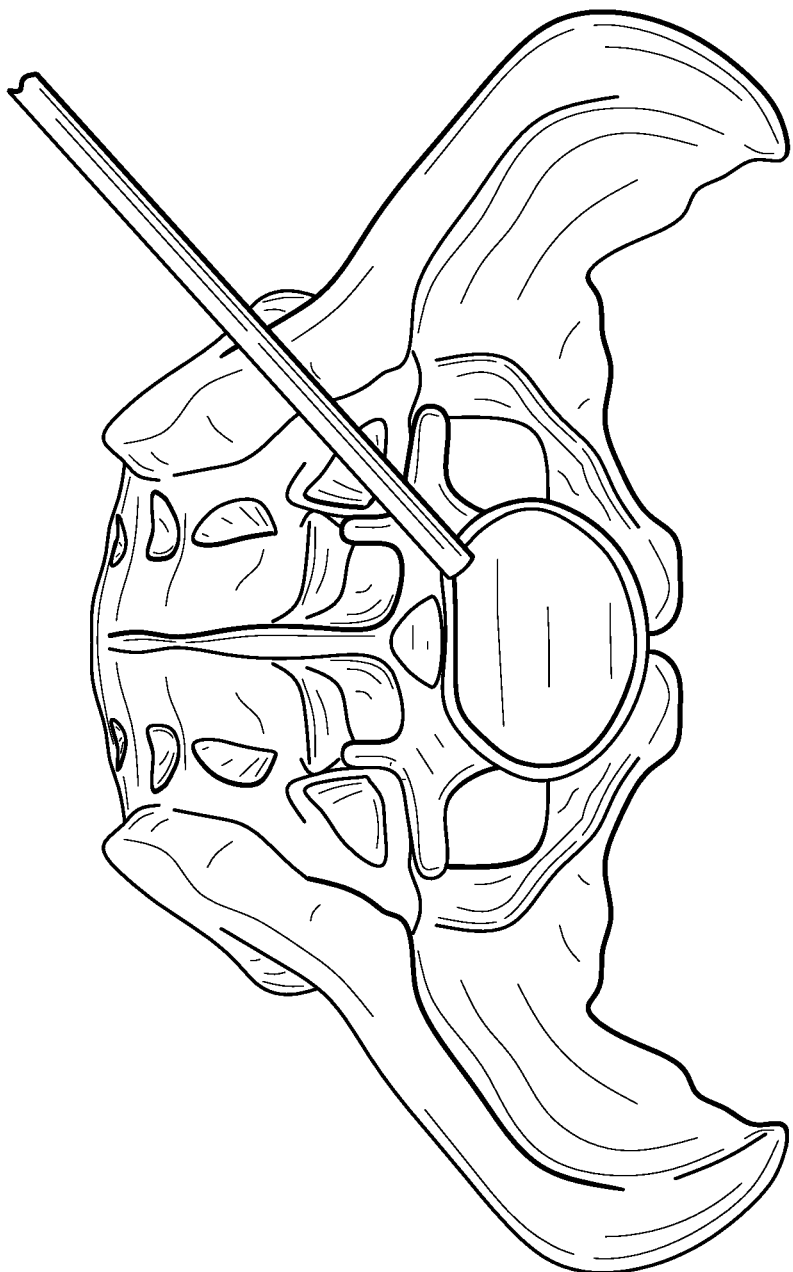

In a first step, and now referring to FIG. 1A, the surgeon removes at least the nucleus pulposus portion of the disc targeted for removal.

Figure 1B:
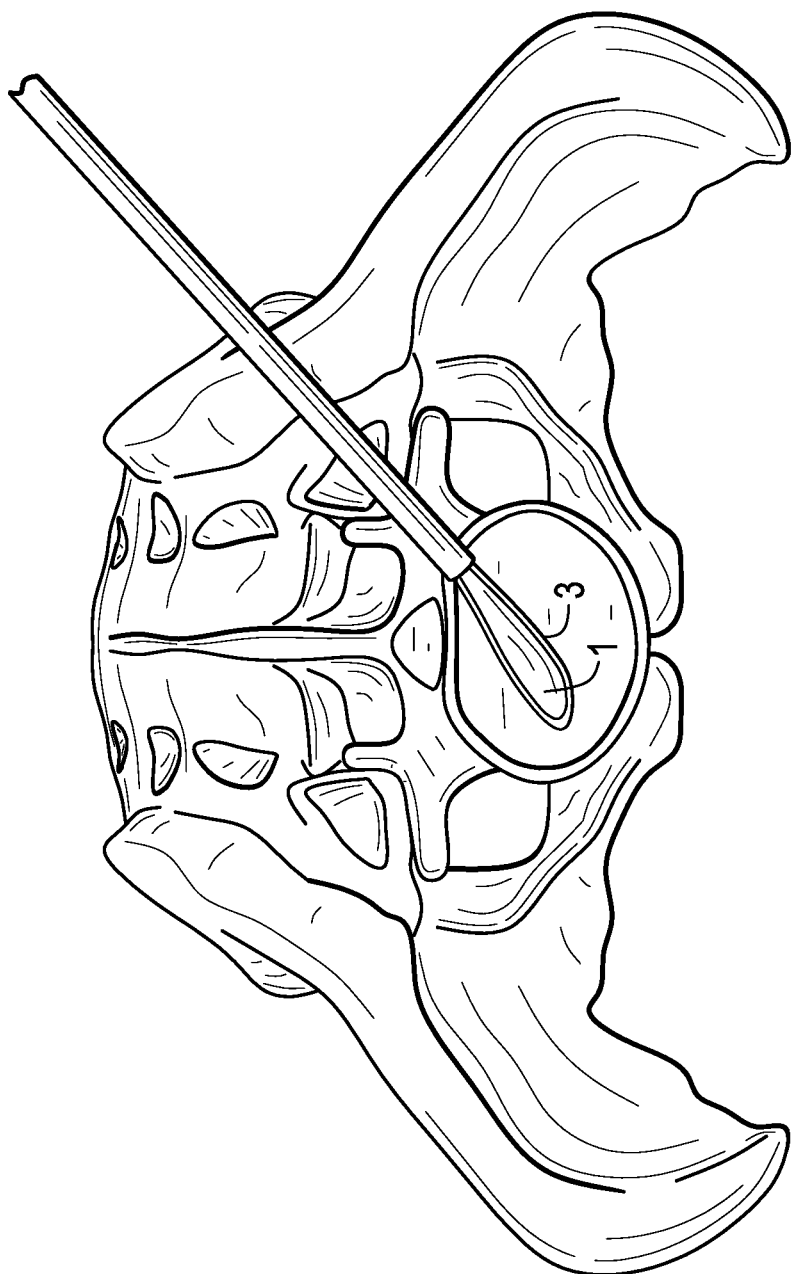

In a second step, and now referring to FIG. 1B, the central inflatable distractor and the perimeter balloon are inserted into the disc space and positioned in the central region thereof. Typically, in this position, the perimeter balloon is wrapped around the central inflatable distractor so that the inner surface of the fusion balloon contacts the outer perimeter of the inflated distractor.

In a third step, and now referring to FIG. 1C, the central inflatable distractor is inflated and thereby separates the vertebral endplates to a designated height.

Figure 1D:
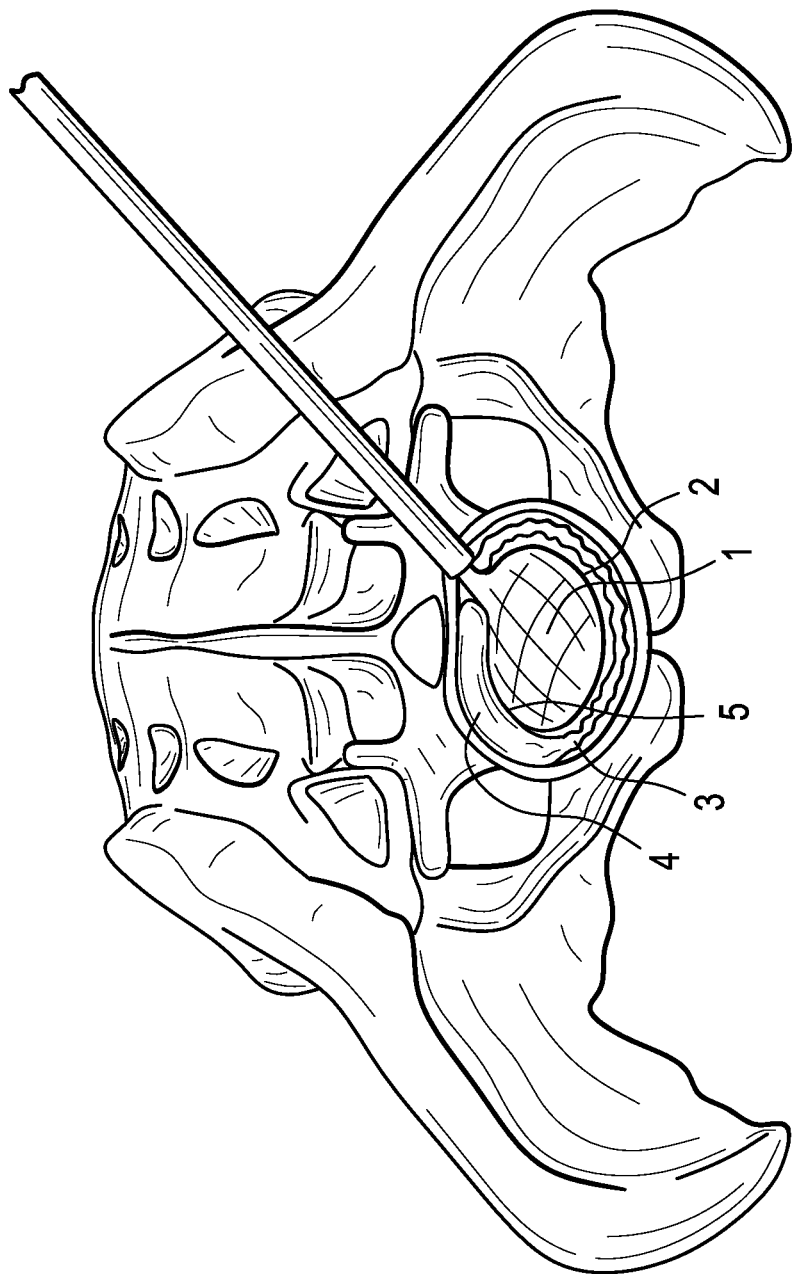

In a fourth step, and now referring to FIG. 1D, a curable material is flowed into the perimeter balloon. The balloon expands around the inflated central distractor to both reach circumferentially around the distractor and to contact the vertebral endplates separated by the distractor. In essence, the filled perimeter balloon takes up all of the void space created by the inflation of the central distractor.

In a fifth step, and now referring to FIG. 1E, the surgeon waits while the curable material cures. In some cases, such as when a conventional PMMA is used, this waiting period may be 5-20 minutes. In some embodiments, the surgeon can accelerate the curing of the curable material by various energy means, including heating it, using a chemical accelerant, light and vibrations.

Figure 1F:
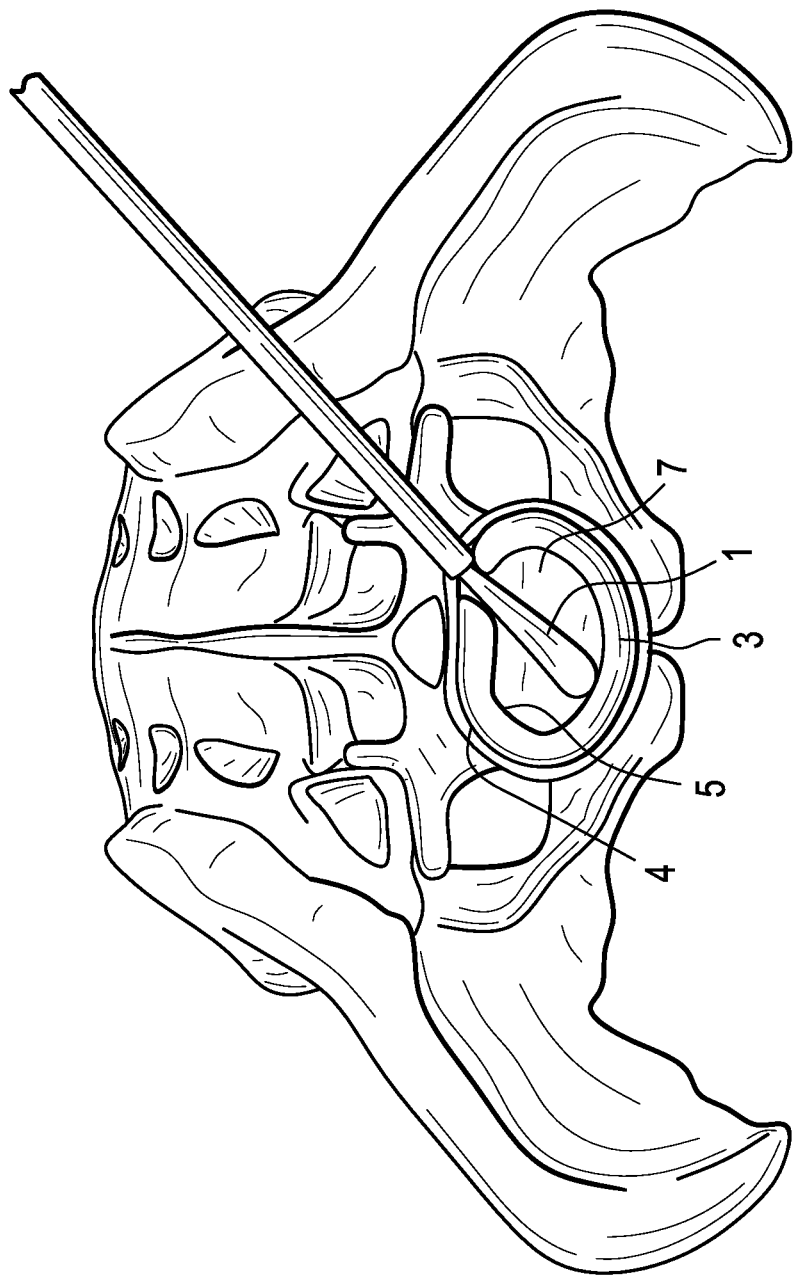

In a fifth step, and now referring to FIG. 1F, the material in the perimeter balloon is fully cured, and the central distractor is deflated.

Figure 1G:
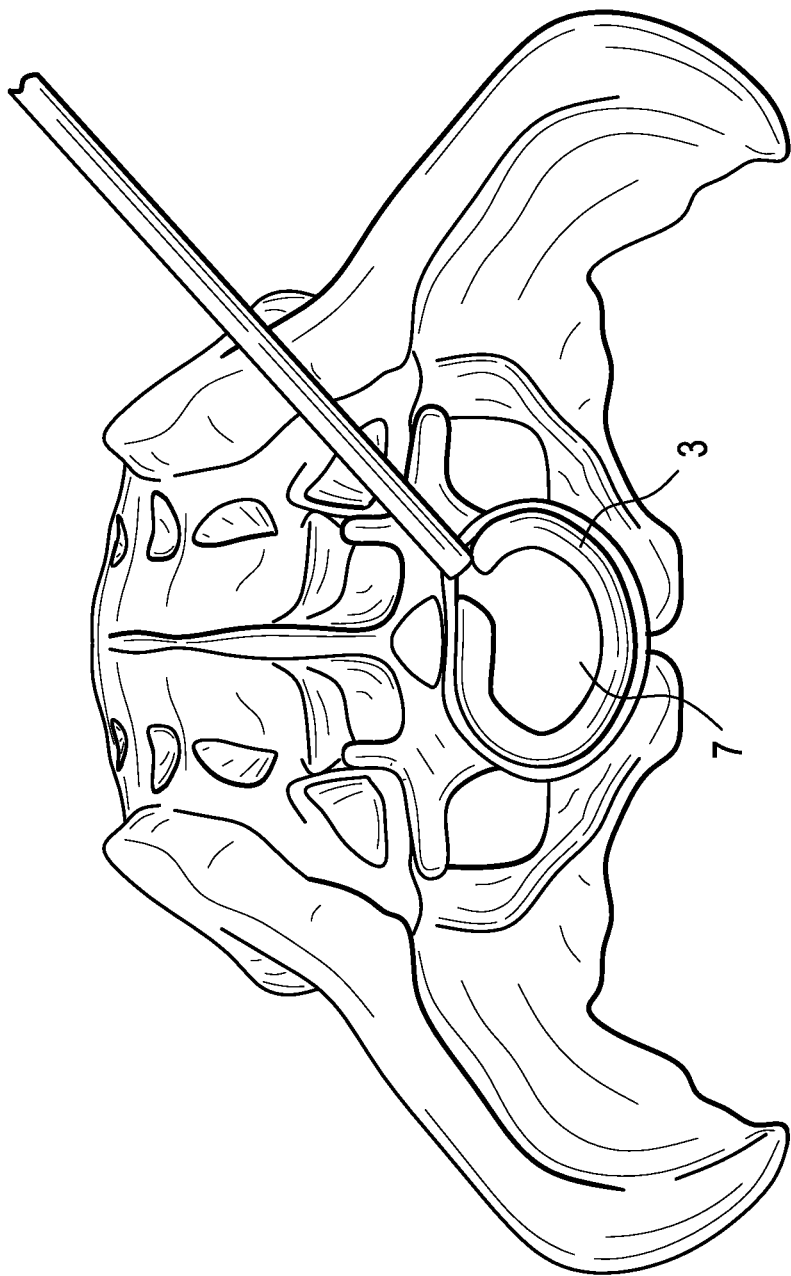

In a sixth step, and now referring to FIG. 1G, the deflated central distractor is withdrawn, thereby leaving a horseshoe-shaped structural support in the disc space. This horseshoe provides support along the cortical rim of the vertebrae while leaving an access point to the center of the disc space.

In a seventh step, and now referring to FIG. 1H, a tube is inserted through the access point produced in the sixth step and positioned near the center of the disc space. Graft material 11 is then flowed through this tube and into the disc space, thereby filling the void with graft.

In FIG. 1I, the graft fill tube is removed.

Therefore in accordance with the present invention, there is provided of treating an intervertebral disc space, comprising the steps of:
a) introducing an inflatable distractor into a disc space in an uninflated form,
b) inflating the inflatable distractor with a biologically inert fluid to distract the disc space,
c) introducing an inflatable balloon into the disc space,
d) filling the inflatable balloon with a curable material;
e) deflating the inflated distractor after the curable material has cured to produce an inner space;
f) removing the deflated distractor from the disc space; and
g) filling the inner space with an osteogenic material.

Therefore in accordance with the present invention and now referring to FIG. 1E, there is provided an instrument for forming an intervertebral fusion device comprising:
a) a distraction device comprising i) a first tube 21 having a distal end portion 23 and ii) an inflatable distractor 1 attached to the distal end portion of the first tube, wherein the inflatable distractor is filled with a biological inert fluid,
b) a fusion assembly comprising i) a second tube 25 having a distal end portion 27 and ii) an inflatable balloon 3 attached to the distal end portion of the second tube, wherein the inflatable balloon is filled with a curable material and has a height sized to span a disc space,
wherein the distal end portion of the first tube is substantially adjacent the distal end portion of the second tube.

Therefore in accordance with the present invention and now referring to FIG. 1D, there is provided balloon assembly for treating an intervertebral disc space, comprising:
a) an inflated distractor 1 having an outer perimeter 2 and being sized to distract the intervertebral disc space, the inflated distractor filled with a biologically inert fluid, b) an inflated fusion balloon 3 forming a shape having an outer perimeter 4 and an inner surface 5, the fusion balloon filled with a curable material, wherein the balloon wraps around the distractor so that the inner surface of the fusion balloon contacts the outer perimeter of the inflated distractor, wherein the balloon forms an annular shape defining an inner space and the inflated distractor is disposed in the inner space.

Therefore in accordance with the present invention and now referring to FIG. 1F, there is provided balloon assembly for treating an intervertebral disc space, comprising:

a) a deflated distractor 1 having an outer perimeter, b) an inflated fusion balloon 3 forming a shape having an outer perimeter 4 and an inner surface 5 defining an inner space 7, the fusion balloon filled with a cured material, the balloon being sized to distract the intervertebral disc space, wherein the deflated distractor is disposed within the inner space of the balloon.

The purpose of the inflatable distractor is to distract the collapsed disc space to a desirable height that restores the physiologic spatial relationship of the adjacent vertebral bodies. The inflatable distractor balloon may be provided in a multiplicity of sizes to correspond to appropriate disc heights. In some expanded embodiments, the central inflatable distractor has a cylindrical shape comprising an annular intermediate portion between two endfaces. In some expanded embodiments, the space within the annular intermediate portion is filled with a biologically inert distraction fluid, such as saline. The endfaces may have roughened outer surfaces in order to better grip the vertebral endplates. In some embodiments, the endfaces are substantially parallel to each other in the inflated condition. In others, the endfaces form an angle with each other (such as being 5 and 20 degrees) in order to provide a desirable amount of lordosis to the disc space. The central inflatable distractor may be made from the balloon materials disclosed in US Patent Publication 2004-0230309, the specification of which is incorporated by reference in its entirety.

The perimeter balloon can be made of any conventional material used for medical balloons. In some embodiments, it can be nonporous. In other embodiments, it can be porous to allow some cement to escape and thereby bond the support to the adjacent tissue. In some embodiments, the perimeter balloon is resorbable over time. The upper and lower surfaces of the perimeter balloon may have roughened outer surfaces in order to better grip the vertebral endplates. These roughened outer surfaces may include for example, a plurality of teeth. The balloon may be made from the balloon materials disclosed in US Patent Publication 2004-0230309, the specification of which is incorporated by reference in its entirety.

In one embodiment, the perimeter balloon is made of an elastic material. This allows the balloon to be form-fitting as it expands into the space between the central inflatable distractor and the surviving annulus fibrosus. In other embodiments, the balloon is inelastic and forms a predetermined shape when inflated. Such an inelastic balloon may be beneficial because the predetermined shape can be a horseshoe shape, and thereby allow the structural support to extend around the perimeter of the central inflatable distractor and rest upon the cortical rim.

In other embodiments, the perimeter balloon forms a substantially horseshoe-shape. The horseshoe shape is advantageous because it provides for a large surface area to rest upon the cortical rim of the adjacent vertebral bodies, and its open end allows for both withdrawal of the central deflated distractor and delivery of the bone graft into the inner space. Preferably, the perimeter balloon is made of a shape memory material that takes on the shape of a horseshoe in its relaxed configuration. In other embodiments, however, the horseshoe shaped perimeter balloon is made of a conventional polymer having no shape memory characteristics, and the balloon is simply manually curled around the central inflatable distractor prior to its delivery into the disc space, so that when the perimeter balloon enters the disc space, it already has a substantially horseshoe shape.

In these horseshoe-shaped embodiments, the curable material may be introduced into the perimeter balloon by a third tube whose distal end is located within the perimeter balloon. The distal end of this third tube is initially fully inserted into the perimeter balloon and begins by filling the distal portion of the perimeter balloon. As curable material fills the distal portion of the perimeter balloon, the distal end of this third tube is withdrawn proximally from the perimeter balloon at the same rate as the rate of fill. This third tube thereby insures the complete filling of the perimeter balloon. In other embodiments, the curable material is simply flowed freeform into the proximal end opening of the perimeter balloon and allowed to fill the perimeter balloon.

Figure 2:
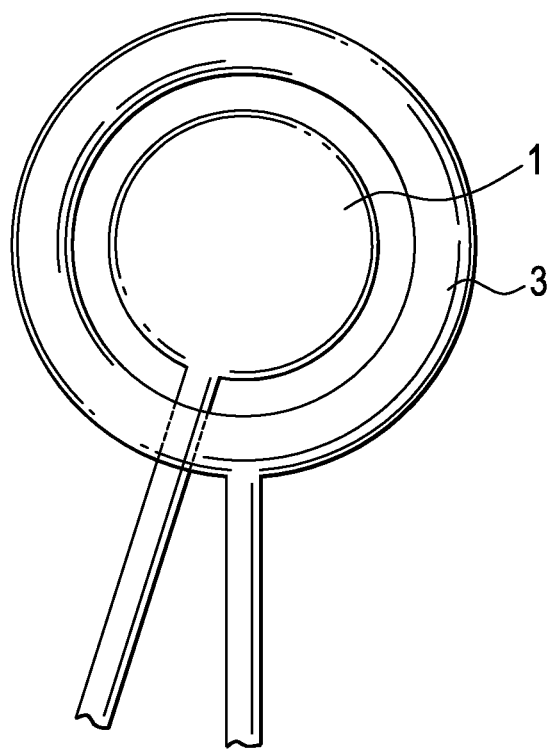
FIG. 2 discloses an annular perimeter balloon of the present invention.

In one embodiment, the perimeter balloon forms an annular shape. An annular perimeter balloon can be accomplished with the technology disclosed in Stalcup's FIG. 4. The Stalcup technology would need to be simply modified by adding a central inflatable distractor at the distal end of Stalcup's first fill hose. Such an annular embodiment is shown in FIG. 2 herein. The annular perimeter balloon possesses a hole that allows for passage and withdrawal of both the central inflatable distractor and a graft fill tube. The advantage of an annular balloon is that it provides slightly more surface area contact with the vertebral bodies than the horseshoe shaped perimeter balloon, thereby reducing the stress upon the structural support. It also provides for more even support, thereby reducing stress heterogeneities.

In some embodiments, the system can be used without a perimeter balloon, thereby allowing the cement to completely conform to the remaining anatomy. In this embodiment, a catheter could be used to evenly deposit the curable material. This catheter can be steerable and independent of the central balloon, or guided by the circumference of the central inflatable distractor via a guidance system such as a channel, track or sleeve. This guidance system around the central inflatable distractor can also be used to guide tools and implants into the disc space. These tools can be used to inspect the disc space, perform additional disc and annulus removal, and place implants.

The curable substance that fills the perimeter balloon forms a structural material capable of withstanding the physiologic axial loads of the spine. In some embodiments, the curable material may be a conventional bone cement, such as a PMMA cement, or a foaming bone cement.

The graft that is deposited within the inner space can be any graft suitable for fusing bone. The quantity of graft needed to fill the inner space may be estimated from the volume of fluid in the central distractor in its inflated configuration. This allows the surgeon to prepare the proper amount of graft and avoid over- or under-packing the inner space.

The delivery method and implant described herein may be suitable for both complete and partial discectomy (i.e., with annulus and ligament intact).

In some embodiments, it may be convenient to house each of the tubes associated with the balloons within a larger cannula. Housing these tubes within this larger cannula may ease the minimally-invasive insertion of the tubes into the patient. Therefore, in accordance with the present invention, there is provided a delivery cannula having a proximal end portion and a distal end portion;

wherein each tube is substantially received in the delivery cannula so that the distal end of the first tube projects from the distal end of the delivery cannula, and the distal end of the second tube projects from the distal end of the delivery cannula.

Another method of simplifying the delivery of two tubes into the disc space is through the use of a dual lumen tube. A dual lumen tube has two bores that share the same medial wall. Therefore, in some embodiments, the first and second tubes are portions of a dual lumen tube.

In some embodiments, the graft material may be HEALOS FX, a flowable collagen-based material available from DePuy Spine of Raynham, Mass., USA.

In some embodiments, the graft material may comprises a bone forming agent. In some embodiments, the bone forming agent is a growth factor. As used herein, the term "growth factor" encompasses any cellular product that modulates the growth or differentiation of other cells, particularly connective tissue progenitor cells. The growth factors that may be used in accordance with the present invention include, but are not limited to, members of the fibroblast growth factor family, including acidic and basic fibroblast growth factor (FGF-1 and FGF-2) and FGF-4; members of the platelet-derived growth factor (PDGF) family, including PDGF-AB, PDGF-BB and PDGF-AA; EGFs; VEGF; members of the insulin-like growth factor (IGF) family, including IGF-I and -II; the TGF-β superfamily, including TGF-β1, 2 and 3; osteoid-inducing factor (OIF), angiogenin(s); endothelins; hepatocyte growth factor and keratinocyte growth factor; members of the bone morphogenetic proteins (BMPs) BMP-1, BMP-3, BMP-2, OP-1, BMP-2A, BMP-2B, BMP-7 and BMP-14, including HBGF-1 and HBGF-2; growth differentiation factors (GDFs), members of the hedgehog family of proteins, including indian, sonic and desert hedgehog; ADMP-1; bone-forming members of the interleukin (IL) family; rhGDF-5; and members of the colony-stimulating factor (CSF) family, including CSF-1, G-CSF, and GM-CSF; and isoforms thereof.

In some embodiments, platelet concentrate is provided as the bone forming agent. In one embodiment, the growth factors released by the platelets are present in an amount at least two-fold (e.g., four-fold) greater than the amount found in the blood from which the platelets were taken. In some embodiments, the platelet concentrate is autologous. In some embodiments, the platelet concentrate is platelet rich plasma (PRP). PRP is advantageous because it contains growth factors that can restimulate the growth of the bone, and because its fibrin matrix provides a suitable scaffold for new tissue growth.

In some embodiments, the bone forming agent comprises an effective amount of a bone morphogenic protein (BMP). BMPs beneficially increasing bone formation by promoting the differentiation of mesenchymal stem cells (MSCs) into osteoblasts and their proliferation.

In some embodiments, between about 1 ng and about 10 mg of BMP are administered into the target disc space. In some embodiments, between about 1 microgram (µg) and about 1 mg of BMP are administered into the target disc space.

In many preferred embodiments, the bone forming agent is a porous matrix, and is preferably injectable.

The porous matrix of the present invention may contain porous or semi-porous collagen, extracellular matrices, metals (such as Ti, Ti64, CoCr, and stainless steel), polymers (such as PEEK, polyethylene, polypropylene, and PET) resorbable polymers (such as PLA, PDA, PEO, PEG, PVA, and capralactides), bone substitutes (such as TCP, HA, and CaP), autograft, allograft, xenograft, and/or blends thereof. Matrices may be orientated to enable flow from bony attachment locations to the aspiration port. Matrices may be layered with varying densities, pore structures, materials to enable increase stem filter at desired locations via density, pore size, affinity, as well as fluid flow control (laminar, turbilant, and/or tortuous path).

In some embodiments, the porous matrix is a mineral. In one embodiment, this mineral comprises calcium and phosphorus. In some embodiments, the mineral is selected from the group consisting of calcium phosphate, tricalcium phosphate and hydroxyapatite. In one embodiment, the average porosity of the matrix is between about 20 and about 500 µm, for example, between about 50 and about 250 µm. In yet other embodiments of the present invention, in situ porosity is produced in the injected matrix to produce a porous scaffold in the interbody space. Once the in situ porosity is produced in the space, the surgeon can inject other therapeutic compounds into the porosity, thereby treating the surrounding tissues and enhancing the remodeling process of the target tissue.

In some embodiments, the mineral is administered in a granule form. It is believed that the administration of granular minerals promotes the formation of the bone growth around the minerals such that osteointegration occurs.

In some embodiments, the mineral is administered in a settable-paste form. In this condition, the paste sets up in vivo, and thereby immediately imparts post-treatment mechanical support to the interbody space.

In another embodiment, the treatment is delivered via injectable absorbable or non-absorbable cement to the target space. The treatment is formulated using bioabsorbable macro-sphere technologies, such that it will allow the release of the bone forming agent. The cement will provide the initial stability required to treat pain in target tissues. In some embodiments, the cement is selected from the group consisting of calcium phosphate, tricalcium phosphate and hydroxyapatite. In other embodiments, the cement is any hard biocompatible cement, including PMMA, processed autogenous and allograft bone. Hydroxylapatite is a preferred cement because of its strength and biological profile. Tricalcium phosphate may also be used alone or in combination with hydroxylapatite, particularly if some degree of resorption is desired in the cement.

In some embodiments, the porous matrix comprises a resorbable polymeric material.

In some embodiments, the bone forming agent comprises an injectable precursor fluid that produces the in situ formation of a mineralized collagen composite. In some embodiments, the injectable precursor fluid comprises:
 a) a first formulation comprising an acid-soluble type I collagen solution (preferably between about 1 mg/ml and about 7 mg/ml collagen) and
 b) a second formulation comprising liposomes containing calcium and phosphate.

Combining the acid-soluble collagen solution with the calcium- and phosphate-loaded liposomes results in a liposome/collagen precursor fluid, which, when heated from room temperature to 37° C., forms a mineralized collagen gel.

In some embodiments, the liposomes are loaded with dipalmitoylphosphatidylcholine (90 mol %) and dimyristoyl phosphatidylcholine (10 mol %). These liposomes are stable at room temperature but form calcium phosphate mineral when heated above 35° C., a consequence of the release of entrapped salts at the lipid chain melting transition. One such technology is disclosed in Pederson, *Biomaterials* 24: 4881-4890 (2003), the specification of which is incorporated herein by reference in its entirety.

Alternatively, the in situ mineralization of collagen could be achieved by an increase in temperature achieved by other types of reactions including, but not limited to, chemical, enzymatic, magnetic, electric, vibration, focused ultrasound, photo- or nuclear. Suitable sources thereof include light, chemical reaction, enzymatically controlled reaction and an electric wire embedded in the material. To further elucidate the electric wire approach, a wire can first be embedded in the space, heated to create the calcium deposition, and then withdrawn. In some embodiments, this wire may be a shape memory such as nitinol that can form the shape. Alternatively, an electrically-conducting polymer can be selected as the temperature raising element. This polymer is heated to form the collagen, and is then subject to disintegration and resorption in situ, thereby providing space adjacent the mineralized collagen for the bone to form.

In some embodiments, the osteoconductive material comprises calcium and phosphorus. In some embodiments, the osteoconductive material comprises hydroxyapatite. In some embodiments, the osteoconductive material comprises collagen. In some embodiments, the osteoconductive material is in a particulate form.

Specific matrices may be incorporated into the device to provide load bearing qualities, enable directional bone formation, and/or control density of regenerated bone (cortical vs cancellous) or enable cell formation for soft tissue attachment. Nanotubes or nanocrystals can be orientated in a generally axial direction to provide for load bearing abilities as well as capillary wicking of vascular flow to further enhance directional bone formation. Biocompatible nanotubes can currently be produced from either carbon or titanium or bone substitutes including Ca, HA, and TCP.

In one embodiment, the bone forming agent is a plurality of viable ex vivo osteoprogenitor cells. Such viable cells, introduced into the interbody space, have the capability of at least partially supplementing the in situ drawn stem cells in the generation of new bone for the interbody space.

In some embodiments, these cells are obtained from another human individual (allograft), while in other embodiments, the cells are obtained from the same individual (autograft). In some embodiments, the cells are taken from bone tissue, while in others, the cells are taken from a non-bone tissue (and may, for example, be mesenchymal stem cells, chondrocytes or fibroblasts). In others, autograft osteocytes (such as from the knee, hip, shoulder, finger or ear) may be used.

In one embodiment, when viable ex vivo cells are selected as an additional therapeutic agent or substance, the viable cells comprise mesenchymal stem cells (MSCs). MSCs provide a special advantage for administration into the interbody space because it is believed that they can more readily survive the relatively harsh environment present in the space; that they have a desirable level of plasticity; and that they have the ability to proliferate and differentiate into the desired cells.

In some embodiments, the mesenchymal stem cells are obtained from bone marrow, such as autologous bone marrow. In others, the mesenchymal stem cells are obtained from adipose tissue, preferably autologous adipose tissue.

In some embodiments, the mesenchymal stem cells injected into the interbody space are provided in an unconcentrated form, e.g., from fresh bone marrow. In others, they are provided in a concentrated form. When provided in concentrated form, they can be uncultured. Uncultured, concentrated MSCs can be readily obtained by centrifugation, filtration, or immuno-absorption. When filtration is selected, the methods disclosed in U.S. Pat. No. 6,049,026 ("Muschler"), the specification of which is incorporated herein by reference in its entirety, can be used. In some embodiments, the matrix used to filter and concentrate the MSCs is also administered into the interbody space.

In some embodiments, bone cells (which may be from either an allogeneic or an autologous source) or mesenchymal stem cells, may be genetically modified to produce an osteoinductive bone anabolic agent which could be chosen from the list of growth factors named herein. The production of these osteopromotive agents may lead to bone growth.

Recent work has shown that plasmid DNA will not elicit an inflammatory response as does the use of viral vectors. Genes encoding bone (anabolic) agents such as BMP may be efficacious if injected into the uncoupled resorbing bone. In addition, overexpression of any of the growth factors provided herein or other agents which would limit local osteoclast activity would have positive effects on bone growth. In one embodiment, the plasmid contains the genetic code for human TGF-$\beta$ or erythropoietin (EPO).

Accordingly, in some embodiments, the additional therapeutic agent is selected from the group consisting of viable cells and plasmid DNA.

A matrix may be made from hydrogels or may incorporate a hydrogel as component of the final structure. A hydrogel may be used to expand and enhance filling, improve handling characteristics or increase vacuum pressure. The increased vacuum pressure may be used to determine adequate hydration/stem cell filtration.

In all cases, excess bone marrow aspirate can be collected and mixed with added graft extenders including collagen like the HEALOS™, and HEALOS FX™, each of which is available from DePuy Spine Inc, Raynham, Mass., USA.

Figure 3A:
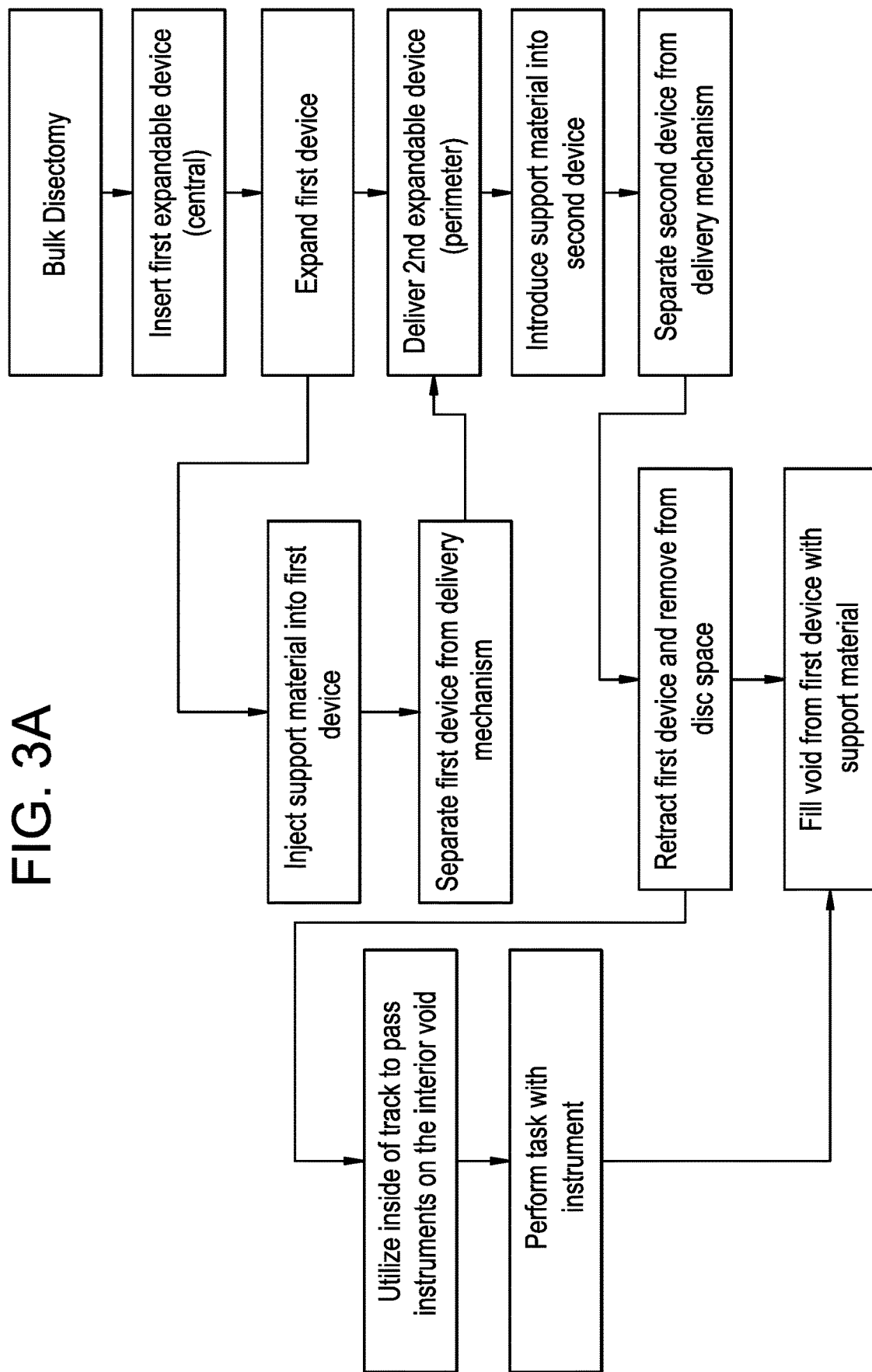
FIGS. 3A & 3B disclose flow charts for preferred steps of the method of the present invention.

Now referring to FIG. 3a, there is provided a flow chart of some preferred methods of carrying out the present invention. In general, this FIG. discloses the steps of:
a) removing disc tissue to create a disc space (bulk discectomy);
b) inserting the central inflatable distractor into the disc space;
c) expanding the central inflatable distractor;
d) inserting the perimeter balloon into the disc space;
e) introducing a curable material into the perimeter balloon, and)
f) separating the perimeter balloon from its second delivery tube.

In step c) above, the step of expanding can include injecting a flowable support material (instead of saline) into the central inflatable distractor. The flowable support material can be selected from the group consisting of graft, hydrogels, curable materials, artificial disc materials, autograft and allograft. This injecting step can be followed by a step of separating the central inflatable distractor from its (first) delivery tube so that it may remain in the disc space.

In some embodiments; after step f), there may be a further step of:

g) retracting the central inflatable distractor and removing it from the disc space to create an inner space.

In one embodiment, step g) may be followed by a step of:

h) filling the inner space with a flowable support material. The flowable support material can be selected from the group consisting of graft, hydrogels, curable materials, artificial disc materials, autograft and allograft.

In another embodiment, removal of the central inflatable distractor (step g)) may be followed by:

i) passing an instrument into the inner space, and
ii) performing a task with the instrument.

The passing of the instrument into the inner space may be accomplished by utilizing a track located upon the inner face of the perimeter balloon. The instrument may be selected from the group consisting of a camera, a light, a scraper, suction, irrigation, a rasp, a knife, grasping, a burr, and a rotary cutter. The task may be selected from the group consisting of inspection, disc removal, and endplate preparation. Performance of the task may be followed by a step of:

a) filling the inner space with a flowable support material.

The perimeter balloon may then be separated from its delivery tube by cutting, unscrewing or breaking away.

Figure 3B:
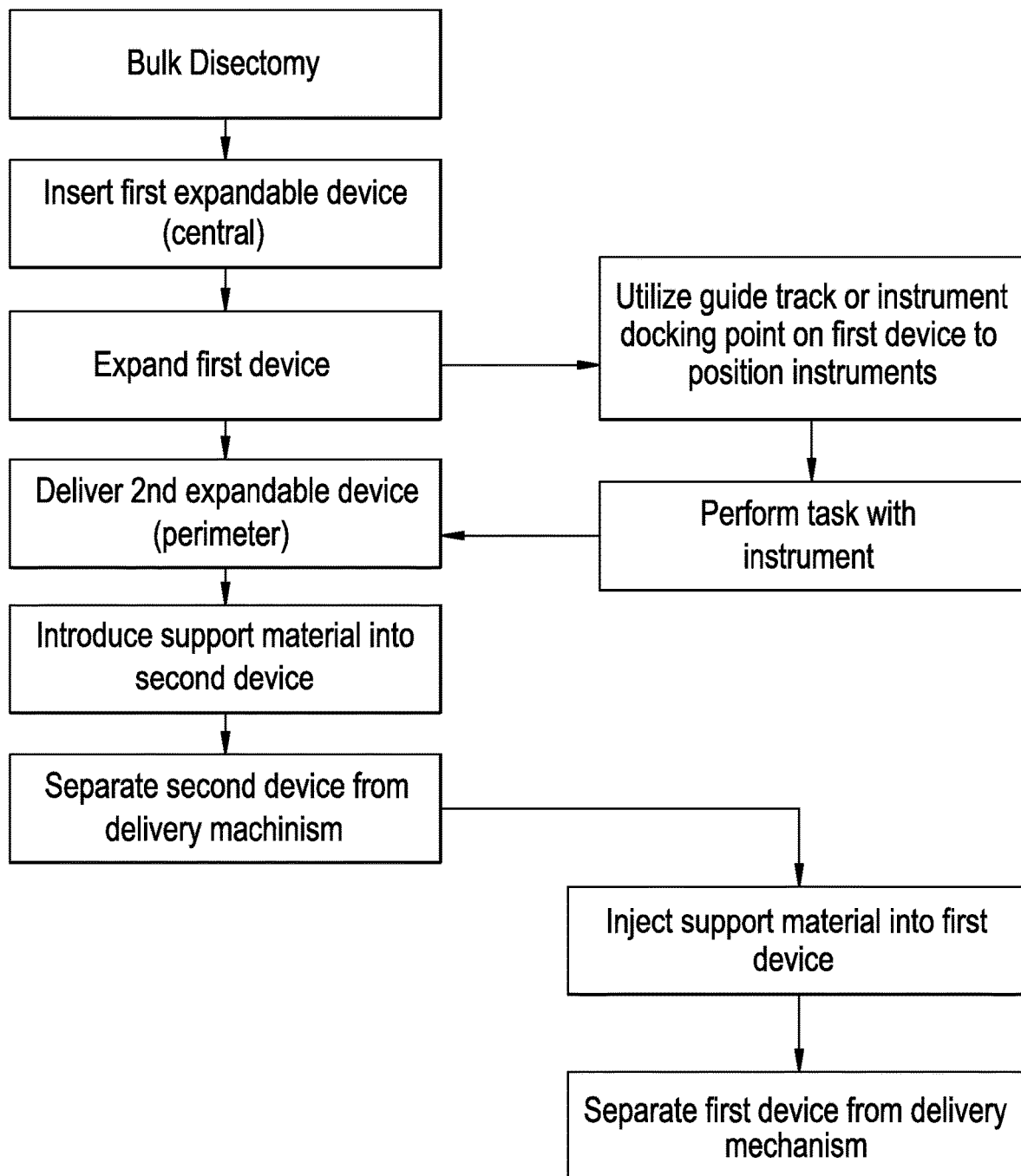

Now referring to FIG. 3b, there is provided a flow chart of some other preferred methods of carrying out the present invention. In general, this FIG. discloses the steps of:

a) removing disc tissue to create a disc space (bulk discectomy);
b) inserting the central inflatable distractor into the disc space;
c) expanding the central inflatable distractor;
d) inserting the perimeter balloon into the disc space;
e) introducing a curable material into the perimeter balloon, and
f) separating the perimeter balloon from its second delivery tube.

Expanding the central inflatable distractor (step c)) may be followed by:

i) passing an instrument into the disc space, and
ii) performing a task with the instrument.

The passing of the instrument into the disc space may be accomplished by utilizing a track located upon the outer face of the central inflatable distractor. Instruments can be passed on both sides of the central inflatable distractor. The instrument may be selected from the group consisting of a camera, a light, a scraper, suction; irrigation, a rasp, a knife, grasping, a burr, and a rotary cutter. The task may be selected from the group consisting of inspection, disc removal, endplate preparation, cutting the annulus, cutting the ALL, cutting the PLL, and direct decompression. Performance of the task may be followed by step d)—inserting the perimeter balloon into the disc space. The delivery of this balloon may also be accomplished by use of the track.

The curable material of step e) can be selected from the group consisting of graft, hydrogels, curable materials, artificial disc materials, autograft and allograft.

The separation of step f) can be accomplished by cutting, unscrewing or breaking away a section.

In some embodiments, the separation of step f) can be followed by:

g) injecting a support material into the first device.

The support material of step g) can be selected from the group consisting of graft, hydrogels, curable materials, artificial disc materials, autograft and allograft.

In some embodiments, the injection of step g) can be followed by h) separating the central inflatable distractor from its delivery tube (so that it may remain in the disc space).

Figure 4:
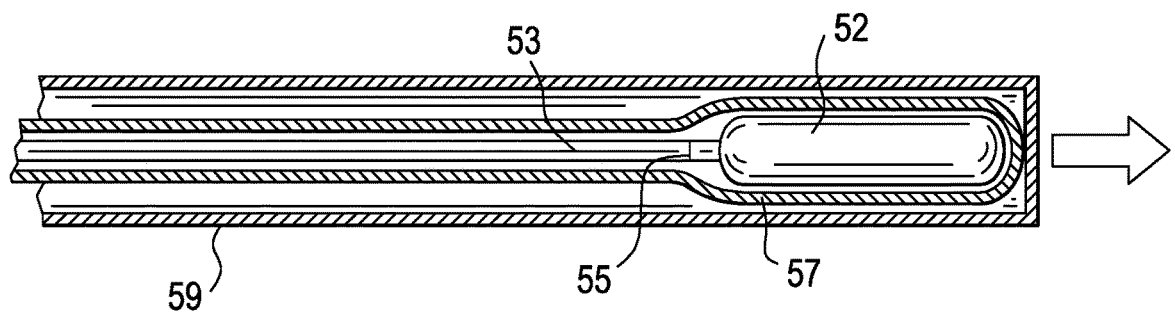
FIG. 4 discloses a cross-section of an MIS delivery of a deflated balloon having a track.

Now referring to FIG. 4, there is provided an embodiment of a balloon having a track associated therewith. Balloon 52 is connected to balloon catheter 53 via connection/release point 55. A track 57 wraps around the periphery of the balloon. This apparatus is disposed within a delivery cannula 59.

Figure 5:
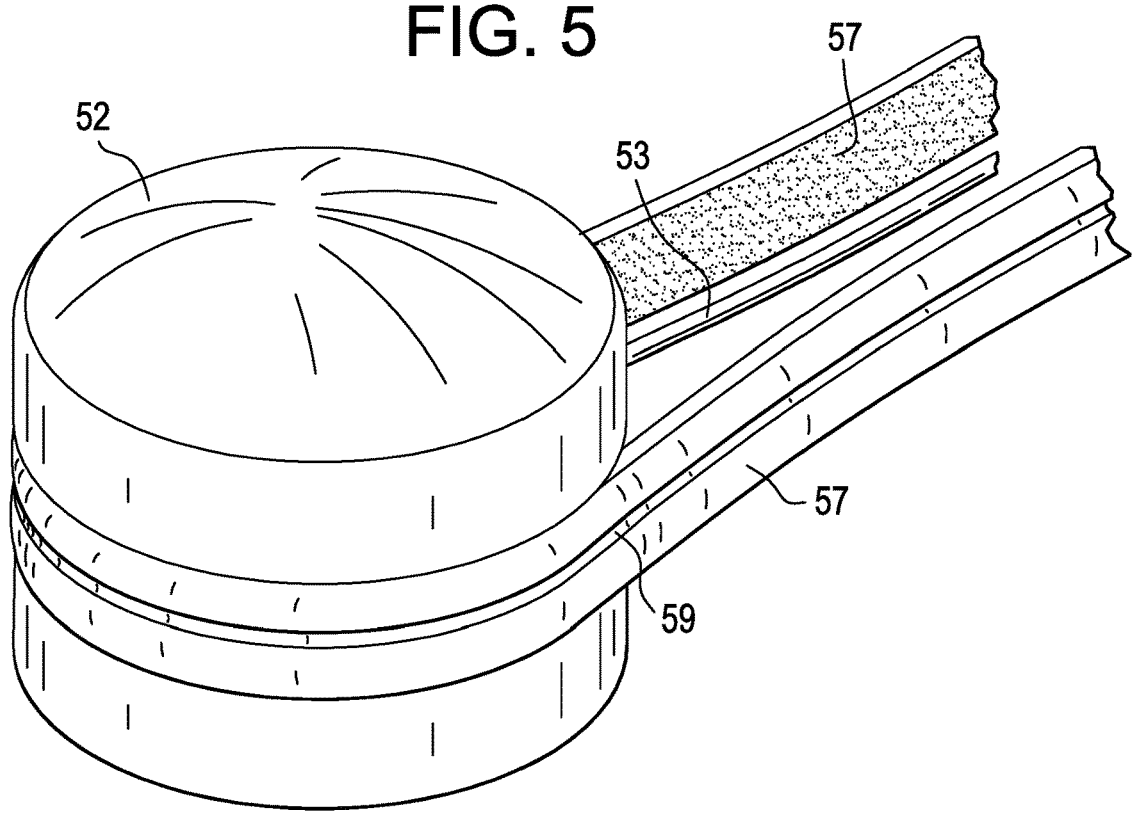
FIG. 5 discloses a perspective view of an inflated balloon having a track.

Now referring to FIG. 5, there is provided a perspective view of a deployed balloon 52 having a track 57. Balloon catheter 53 extends from the proximal portion of the balloon. Track 57 has a central groove 59 for docking with an instrument.

Figure 6A:
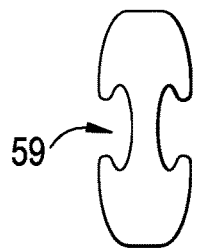
FIGS. 6A-6C disclose cross-sections of tracks of the present invention.
Figure 6B:
Figure 6C:
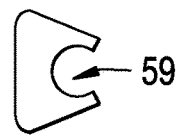
Figure 7:
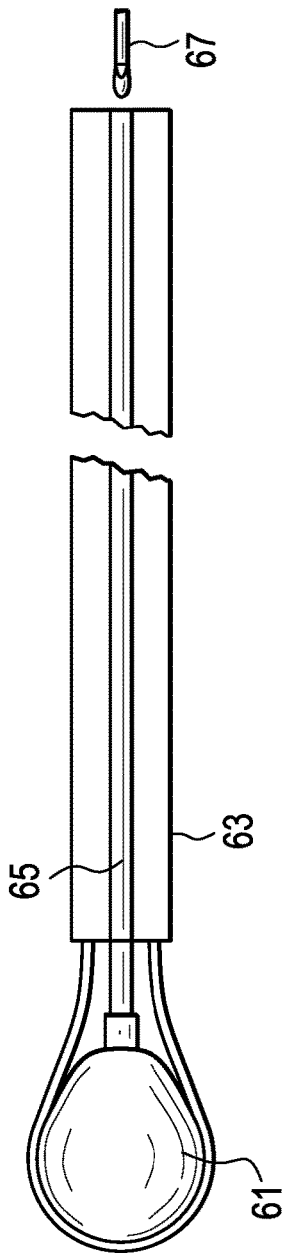
FIG. 7 discloses a balloon of the present invention used as a light source.

FIGS. 6A-6C disclose different track cross sections. FIG. 6A discloses a dual-sided track. FIG. 6B discloses a one-sided track. FIG. 6C discloses a track having a trapezoidal cross-section. FIG. 7 discloses an embodiment in which the central balloon 61 is used as a light source. The balloon is attached to a light-transmitting catheter 65 that is housed within a delivery catheter 63. Light is transmitted from light source 67 into the light-transmitting catheter 65 and then into the balloon 61. In some embodiments, the fluid used to inflate the central balloon can include light-reflecting particles (not shown) in order to better disperse the light. The light allows for easier inspection of the disc space.

Figure 8:
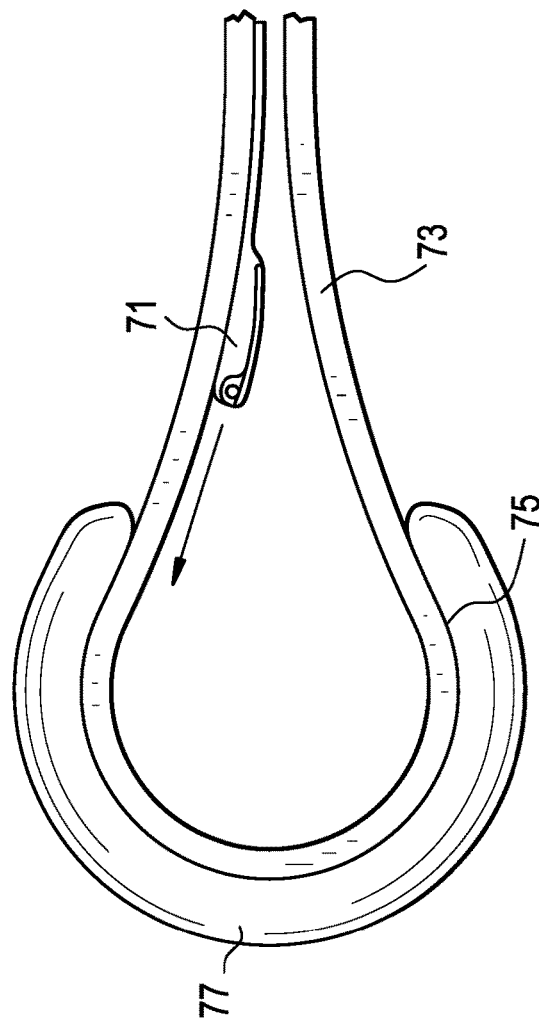
FIG. 8 discloses an assembly for passing instruments into the inner space.

FIG. 8 discloses a step of passing an instrument 71 into the inner space via a track 73 located on an interior surface 75 of the perimeter balloon 77.

Figure 9B:
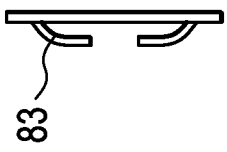
FIGS. 9B-9E disclose cross-section of cutouts of the present invention.
Figure 9A:
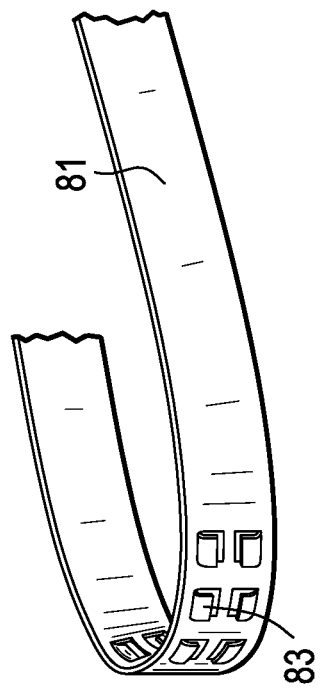
FIG. 9A discloses a track having cutouts.
Figure 9E:
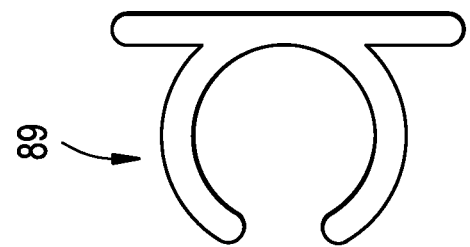
Figure 9D:
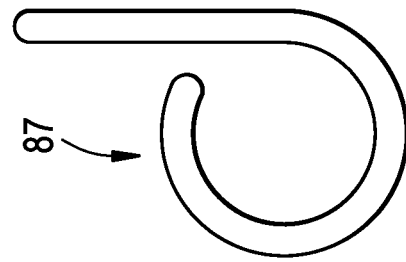
Figure 9C:
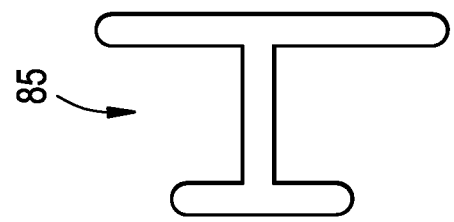

FIG. 9A discloses an embodiment of a track 81 that has cut-outs 83. These cutouts provide a means for securing the instrument. FIG. 9B discloses a cross-section of cutout 83. FIG. 9C discloses a cross-section of a T-Track cutout 85. FIG. 9D discloses a cross-section of a rolled-track cutout 87. FIG. 9E discloses a cross-section of a C-track cutout 89.

Figure 10:
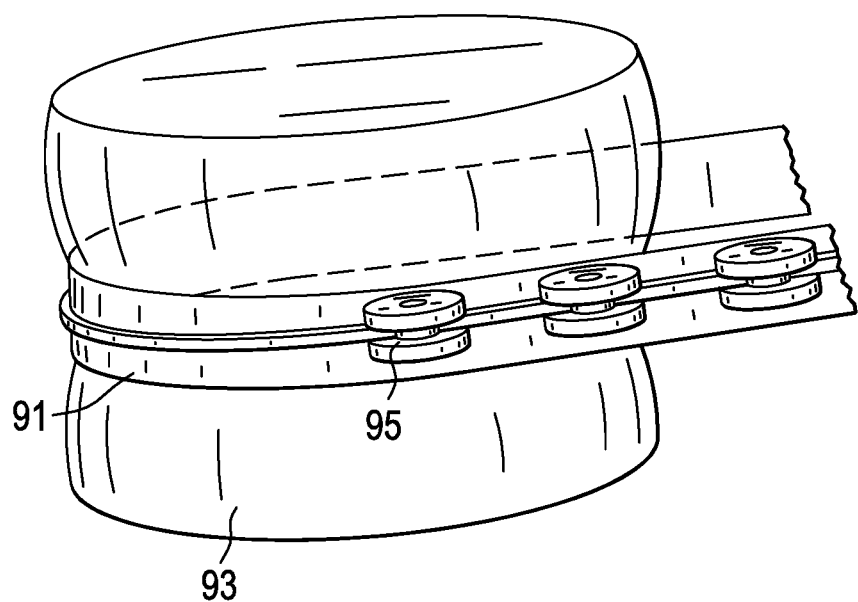
FIG. 10 discloses an inflated balloon having magnetic wheels on its track.

FIG. 10 discloses an embodiment showing means for transporting instruments along a track 91 on the central inflatable balloon 93. A plurality of magnetic wheels 95 are shown travelling along a track. These wheels can be used to transport instruments into and from the disc space.

Figure 11A:
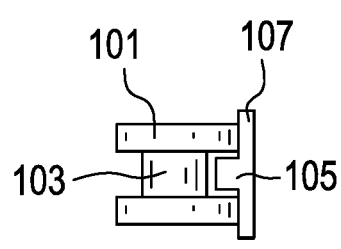
FIGS. 11A-11B disclose cross-sections of magnetic-wheel/track engagement.

FIG. 11A shows details of how the magnetic wheel 101 can be attached to the track. The wheel has a central magnet 103 that contacts central rail 105 of the track 107. The overlap keeps the instrument in line.

Figure 11B:
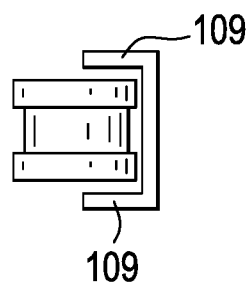

FIG. 11B shows another embodiment of the wheel-track engagement, wherein the track has a pair of side rails 109 that keep the wheel engaged.

FIG. 12 shows a pair of docking ports 111 bilaterally disposed on a central inflatable balloon 113. An instrument 115 can have a distal docking ball 117 for reception by the docking port. In this case, the instrument has an articulating scraper 119 attached thereto for scraping tissue in the disc space.

Now referring back to FIGS. 3A-B, the basic method of carrying out the present invention involves six steps:

Step 1: Bulk Discectomy;
Step 2: Insert first (central) expandable device into the disc space;
Step 3: Expand the first device to distract the disc space;
Step 4: Deliver second (perimeter) expandable device into the disc space;
Step 5: Introduce support material into the second device;
Step 6: Separate second device from the delivery mechanism.

In one optional embodiment, between Steps 3 and 4, support material may be injected into the first (central) device. The support material may be selected from the group consisting of graft, hydrogels, curable materials, artificial disc materials (such as hydrogels), autograft and allograft.

Thereafter, the surgeon can then separate the first device from its associated material delivery tube.

We claim:

1. A method of forming an interbody fusion cage, comprising the steps of;
    a) introducing an inflatable distractor into a disc space in an uninflated form,
    b) inflating the inflatable distractor with a biologically inert fluid comprising saline to distract the disc space,
    c) introducing an inflatable balloon into the disc space,
    d) filling the inflatable balloon with a curable material to define a substantially annular filled balloon having an outer surface, an inner surface,
    e) deflating the inflated distractor after the curable material has cured,
    f) removing the deflated distractor from the disc space, and
    g) filling the inner space with an osteogenic material, wherein the inflatable distractor and the inflatable balloon are introduced into the disc space on opposite sides of a guide that extends proximally out of the disc space.

2. The method of claim 1 wherein the distractor occupies the inner space defined by the balloon.

3. The method of claim 2 wherein the balloon is elastic.

4. The method of claim 2 wherein the balloon is inelastic and forms a predetermined shape when inflated.

5. The method of claim 1 wherein the balloon forms an annular shape.

6. The method of claim 1 wherein the balloon forms a substantially horseshoe-shape.

7. The method of claim 1 wherein the balloon wraps around the distractor so that an inner surface of the fusion balloon contacts an outer perimeter of the inflated distractor.

* * * * *